United States Patent [19]
Jess

[11] 3,993,062
[45] Nov. 23, 1976

[54] HYDROPHOBIC VALVE

[75] Inventor: Thurman S. Jess, Mundelein, Ill.

[73] Assignee: Baxter Laboratories, Inc., Deerfield, Ill.

[22] Filed: Nov. 3, 1975

[21] Appl. No.: 628,276

[52] U.S. Cl. .............................. 128/214 R; 55/159; 128/214 C; 137/183
[51] Int. Cl.² .......................................... A61M 5/14
[58] Field of Search ......... 128/214 C, 214.2, 214 R; 137/183; 55/159; 210/DIG. 23

[56] References Cited
UNITED STATES PATENTS

| | | | |
|---|---|---|---|
| 3,012,569 | 12/1961 | Wooldridge et al. | 137/172 |
| 3,384,089 | 5/1968 | Shriner | 128/350 V |
| 3,631,654 | 1/1972 | Riely et al. | 55/159 |
| 3,854,907 | 12/1974 | Rising | 55/159 |

Primary Examiner—Dalton L. Truluck
Attorney, Agent, or Firm—Paul C. Flattery

[57] ABSTRACT

A hydrophobic valve for use with liquids, such as liquids for intravenous administration comprising a housing provided with inlet and outlet means, both of which communicate with the housing, a resilient, inflatable boot mounted in the housing and positioned to block the flow of liquid through the outlet means when inflated and to permit the flow of liquid through the outlet means when in a deflated position, with the boot including an open portion adjacent to the inlet means which is covered by a hydrophobic filter element capable of repelling liquid but permitting the passage of gases, such as air, therethrough whereby liquid introduced to the housing through the inlet means is passed through the housing for discharge from the outlet means and any air introduced with the liquid is passed through the hydrophobic filter into the boot to stop the flow of liquid from the outlet means when the boot is inflated with the gas.

12 Claims, 5 Drawing Figures

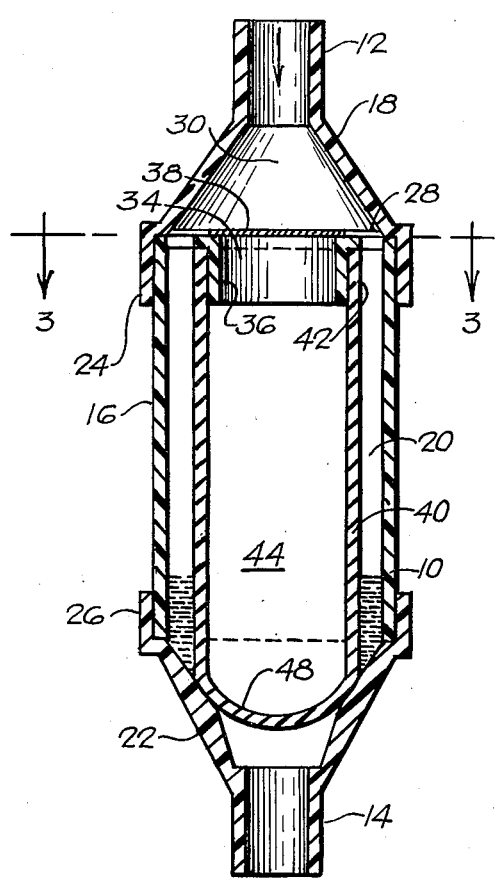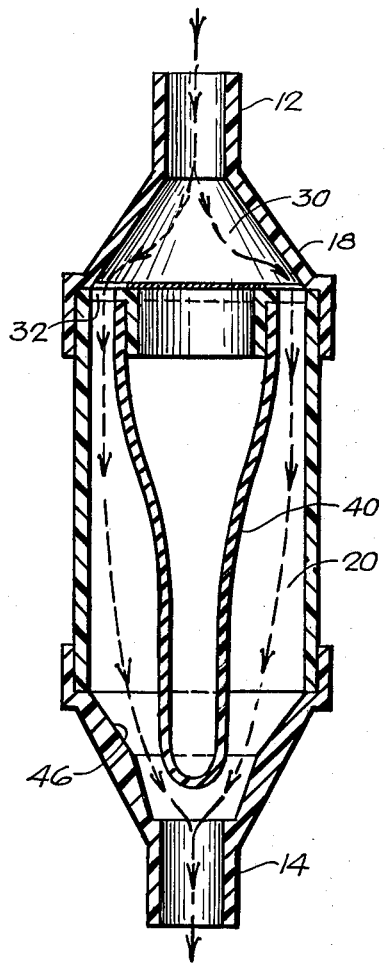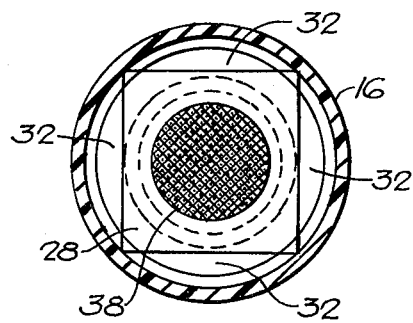

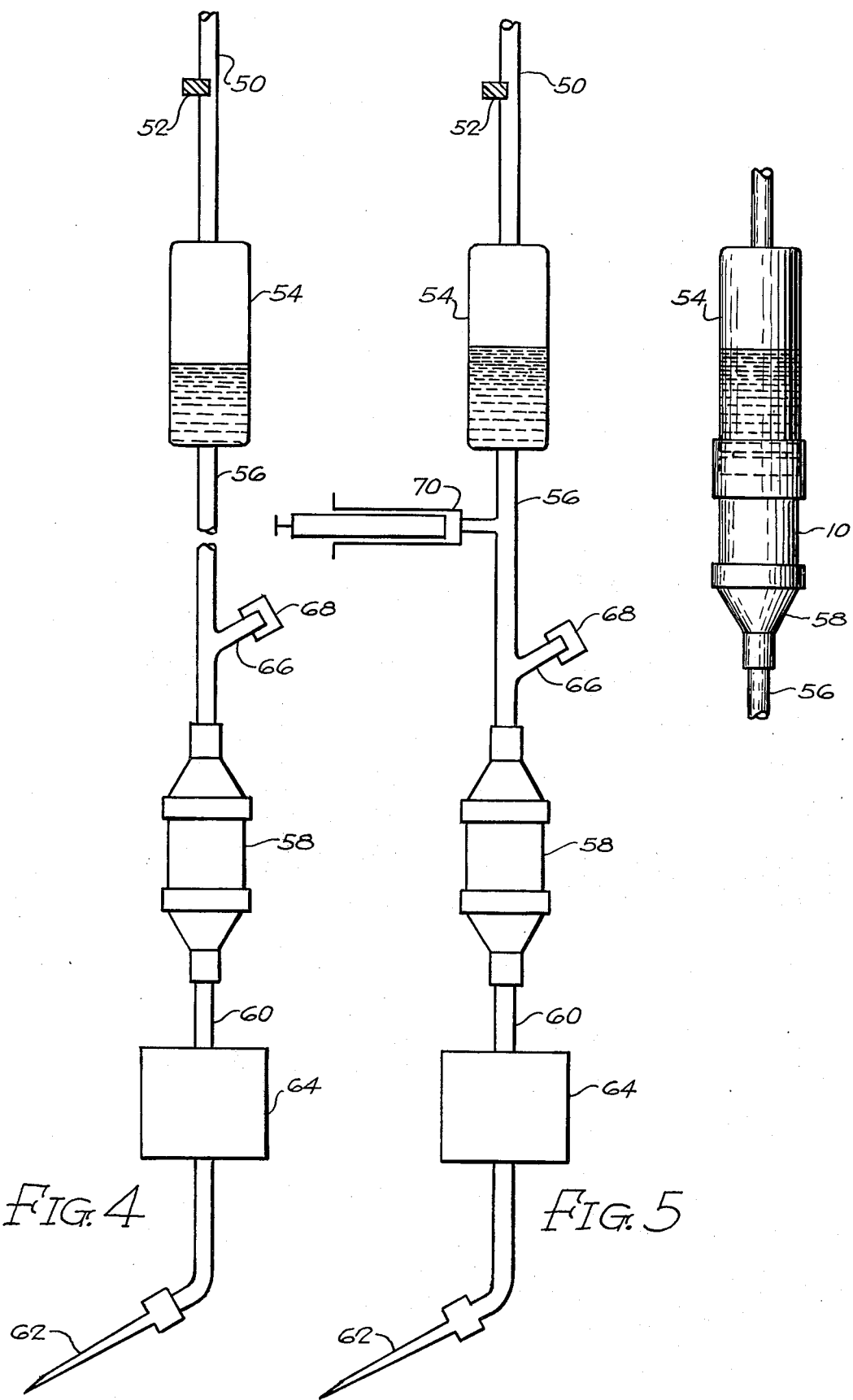

HYDROPHOBIC VALVE

This invention relates to systems for the administration of intravenous liquids, and more particularly to valves for use in such systems.

It is well known in the administration of intravenous liquids that care must be taken to avoid the introduction of air into the system which may be infused to a patient. Various devices have been suggested by the prior art to prevent the infusion of air, known in the art as air embolism. One approach which has been widely used involves the use of a filter which includes a hydrophilic filter element which, when wetted with liquid, is capable of passing liquid therethrough while simultaneously blocking air. One such filter is described in U.S. Pat. No. 3,471,019. The filter described in that patent functions satisfactorily except when, in certain positions, an air bubble present in the filter housing can be caused to spread over the surface of the hydrophilic filter element to thereby effectively cut off further fluid flow. Thus, filters of that type have the disadvantage of being position sensitive, that is, being incapable of proper operation when oriented in certain positions.

Another disadvantage of filters of the type as described in the foregoing patent stems from the fact that no means are provided to stop fluid flow in the event the hydrophilic filter element is ruptured. As will be appreciated by those skilled in the art, a rupture in the hydrophilic filter element allows liquid and any air associated therewith to flow unimpeded through the system.

The prior art has attempted to provide filters which either block or eliminate air in an intravenous administration system which are position insensitive. One such filter is described in U.S. Pat. No. 3,523,408. There, the filter which is described as position insensitive is formed of hydrophobic and hydrophilic filter elements which must be closely spaced together, by a distance of the order of 0.5 to 2 mm to insure that gas bubbles formed between the two filter elements do not cause blockage of liquid flow through the hydrophobic filter element. The necessity for close spacing of the filter element itself represents a distinct disadvantage. In addition, filters of the type described in the latter patent are rendered totally ineffective in the event there is a rupture in the hydrophilic filter element.

It is accordingly an object of the present invention to provide a valve suitable for use with intravenous administration systems which is capable of blocking air from passage therethrough.

It is a more specific object of the invention to provide a hydrophobic valve suitable or use in the intravenous administration of liquids which is capable of blocking air even though the filter element associated therewith may be ruptured during use.

It is yet another object of the invention to provide an intravenous administration system embodying the hydrophobic valve of this invention.

These and other objects and advantages of the invention will appear more fully hereinafter, and, for purposes of illustration but not of limitation, an embodiment of the invention is shown in the accompanying drawings wherein:

FIG. 1 is a side view in section of a valve embodying the features of this invention;

FIG. 2 is a side view in elevation of the embodiment shown in FIG. 1, with the valve in position to permit liquid flow therethrough;

FIG. 3 is a sectional view taken along the lines 3—3 in FIG. 1;

FIG. 4 is a schematic illustration of an intravenous administration set embodying the valve of this invention; and FIG. 5 is a schematic illustration of an alternative embodiment of an intravenous administration set including the valve of this invention.

The concepts of the present invention reside in a valve which includes a resilient, inflatable boot or diaphragm mounted in a housing equipped with both inlet and outlet means. The resilient boot is open at its portion adjacent the inlet means to the housing, and the open portion is covered in a sealing relationship by a hydrophobic filter element capable of repelling liquid but permitting the passage of air through the pores thereof.

When in the deflated state or position, the boot is positioned in the housing such as to permit the passage of liquid through the housing for discharge through the outlet means. However, any air introduced with the liquid through the inlet means is passed through the hydrophobic filter into the boot whereby the boot, when inflated with air having passed through the hydrophobic filter, stops the flow of liquid through the discharge means. In this way, the valve of the present invention causes air or like gases associated with the liquid supplied to the valve through the inlet means to be separated from the liquid and passed into the boot. When the boot becomes inflated with the air or like gas, the boot stops the flow of liquid from the outlet means to thereby prevent the passage of any significant amounts of air through the valve.

The hydrophobic valve of this invention operates independently of the position in which it is oriented, and thus is position insensitive. In addition, if a hole or rupture in the hydrophobic filter element should develop, liquid as well as gases can be passed into the boot to inflate the boot and thereby stop the flow of liquid through the outlet means.

Having described the basic concepts of the present invention, reference is now made to the accompanying drawings for a more detailed description of the invention. There is shown in FIGS. 1 and 2 a hydrophobic valve embodying the features of this invention includng a housing generally designated as 10 and equipped with inlet means 12 through which a liquid is supplied to the housing and outlet means 14 from which liquid is discharged from the housing. The housing 10 includes a generally cylindrical portion designated as 16 which terminates at its upper portion in a frusto-conical portion 18 communicating with the inlet means 12 and the interior chamber 20 of the housing. Similarly, the housing 10 includes a lower frusto-conical portion 22 intermediate the housing and the outlet means 14 and communicating therewith.

As will be appreciated by those skilled in the art, the housing, including frusto-conical portions 18 and 22 as well as the inlet and outlet means 12 and 14, can be made of any desired material. Frequently preferred are rigid plastics which can be molded by known, inexpensive techniques. The frusto-conical portions 18 and 22 can be integral with or separate from the cylindrical portion 16. For example, as is illustrated in FIGS. 1 and 2, the frusto-conical portion 18 is integral with the inlet means 12, and includes a peripheral annular flange 24 adapted to engage the cylindrical portion 16 of the housing 10 in a sealing relationship. The frusto-conical portion 22 includes a similar flange 26 which likewise is engaged with the cylindrical wall of the housing 10 in a sealing relationship.

Positioned within the housing is a hydrophobic filter support member 28 which is most clearly illustrated in FIG. 3 of the drawing. The filter support member 28 can be any desired shape, and is mounted adjacent to the inlet means 12. In the preferred practice of this invention, as shown in FIGS. 1 and 2, the filter support member 28 is mounted on the cylindrical portion 16 of the housing 10 and is secured thereto by the overlaying flange member 24.

The filter support member 28 has a configuration such as to define one or more flow paths between the interior 30 of the frusto-conical portion 18 and the chamber 20 defined by the housing 10. As shown in FIG. 3, the filter support member can be generally square in configuration and dimensioned to correspond to the cross section of the housing 10. In this way, each of the four corners of the filter support member 28 are positioned on the cylindrical portion 16 of the housing 10, with the filter support member 28 and the cylindrical portion 16 defining an opening or flow path 32 bonded on one edge by the lateral edge of the filter support member 28 and on the other edge by the cylindrical portion 16 of the housing 10.

In the preferred practice of the invention as shown in FIGS. 1 and 2, the filter support member 28 includes a generally central opening 34 defined by a downwardly extending annular flange 36. The opening 34 is covered in a sealing relationship by the hydrophobic filter element 38 overlying the support plate 28 or positioned within the opening 34. Such hydrophobic filter elements are, of themselves, known to those skilled in the art; they are capable of repelling liquids while simultaneously passing air or like gases through the pores thereof. Such hydrophobic filter elements are further described in the foregoing U.S. patents.

Mounted on the filter support member 28 is an inflatable boot 40. As is shown in FIG. 1 of the drawing, the inflatable boot is open at its top portion 42, and is mounted on the downwardly projecting annular flange 36 of the filter support member 28. The boot 40 is formed of a material having an elastic memory, preferably an elastomeric material which is capable of being inflated. As is shown in FIG. 1, when the pressure in the chamber 44 defined by the boot 40 equals the pressure in the chamber 20 defined by the housing 10, the boot 40 is inflated so as to engage the frusto-conical portion 22 adjacent the outlet means 14 in a sealing relationship to thereby block the flow of liquid from the chamber 20 through the frusto-conical portion 22 to the outlet means 14. For this purpose, as is perhaps most clearly shown in FIG. 2 of the drawing, the frusto-conical portion 22 includes a beveled valve seat 46 which is dimensioned to correspond to the lower portion 48 of the boot 40 whereby the lower portion 48 forms a fluid tight seal with the valve seat 46.

As is shown is FIG. 2 of the drawing, when the boot 40 is in the deflated state, that is the pressure in the boot 40 being less than the pressure in the chamber 20, no seal is formed between the lower portion of the boot 40 and the valve seat 46 whereby liquid introduced to the inlet means 12 is capable of passage through the chamber 30 defined by the upper frusto-conical portion 18 and through the flow paths 32 into the chamber 20 for passage through the frusto-conical portion 22 for discharge through the outlet means 14.

In the use of the valve of this invention, the boot 40 is collapsed, either manually or mechanically, to expel air from the boot and to permit liquid to flow through the housing 10 including the frusto-conical portion 22 for discharge through outlet means 14 as illustrated in FIG. 2 of the drawing. While the boot is in the deflated state as shown in FIG. 2, the valve is filled with the liquid to be administered and the boot is released. Since the chamber 20 is filled with liquid and only gasses such as air can pass through the hydrophobic filter element 38 into the interior 44 of the boot 40, the boot will remain collapsed as shown in FIG. 2. Any air included with the liquid introduced to the inlet means 12 is drawn through the hydrophobic filter element 38 into the interior 44 of the boot 40. When sufficient air has entered the interior 44 of the 40, the boot 40 will be inflated, that is the pressure in the chamber 44 will be equal to that in the chamber 20, and the lower portion 48 of the boot 40 will again form a seal with the valve set 46 to stop the flow of liquid through the valve. In this way, infusion of air or like gases to the patient can be prevented.

The hydrophobic valve of the present invention can be used with intravenous liquids, including blood and the like. They are preferably used in combination with an intravenous administration set of the type illustrated in FIG. 4 of the drawing. As shown in that figure, the set includes a hollow male connector 50 adapted to be connected to a source of an intravenous liquid (not shown in the drawing). To secure the connector 50 to the source of the liquid, the connector may be provided with a finger grip flange 52. The connector 50 thus communicates with a drip chamber 54 into which the intravenous liquid is allowed to pass. From the drip chamber 54, the intravenous liquid passes through a second tubing means 56 to the valve of this invention 58, such as a valve as shown in FIGS. 1–3. Liquid effluent from the valve passes through tubing means 60 directly to the patient by way of an appropriate needle or like administration means 62 communicating therewith. However, it is likewise possible and sometimes desirable to include with the administration set a filter 64 to filter any particular material from the liquid which has been passed through the valve 58. Since the valve 58 prevents the passage of gases such as air through the system, the filter can simply be a particulate filter.

It is frequently desirable that the intravenous administration set include an injection site for the purpose of enabling medical preparations to be added to the system, independent of the liquid supplied to the drip chamber 54. For this purpose, one of the tubing means, such as the tubing means 56, is provided with a "Y" injection site formed of a branch tube 66 communicating with the tubing means 56 and terminating in an elastomeric injection plug 68 through which a medical preparation can be injected by way of a hypodermic syringe.

In many instances of intravenous administration, it is desirable to employ pump means to control and/or facilitate the delivery of the intravenous liquid to the patient. One such administration system is illustrated in FIG. 5 of the drawing. In that embodiment, the administration set is generally the same as that shown in FIG. 4, except that the conduit means 56 between the drip chamber 54 and the valve 58 of this invention includes pump means generally designated as 70. In the embodiment illustrated in FIG. 5, the pump means 70 is schematically shown as a syringe pump, the details of which are well known to those skilled in the art. As will also be appreciated by those skilled in the art, the syringe may be mechanically driven, or, alternatively, may be replaced by any of a variety of conventional mechanical pumps commercially available for pumping intravenous liquids.

It is also desirable in some instances to incorporate the hydrophobic valve of this invention into a drip chamber. For this purpose, the frusto-conical portion 18 at the top of the housing 10 can simply be omitted. In this variation of the invention, it is preferable to extend the cylindrical wall 16 of the housing 10 upwardly so as to define a drip chamber of the type shown in FIGS. 4 and 5, but having the hydrophobic value toward the bottom thereof. In this way, the hydrophobic value of this invention shuts off liquid flow from the drip chamber embodying the hydrophobic valve when the source of the intravenous liquid supplying the drip chamber empties. Flow of intravenous liquid through the drip chamber can simply be restarted by providing a fresh source of intravenous liquid and deflating the boot, thereby completely avoiding repriming of the set.

It will be understood that various changes and modifications can be made in the details of construction, procedure and use without departing from the spirit of the invention, especially as defined in the following claims.

I claim:

1. A hydrophobic value for liquids comprising:
   a. a housing defining inlet means and outlet means, each of the inlet and outlet means communicating with the housing
   b. a resilient, inflatable boot mounted in the housing, said boot positioned to block the flow of liquid through the outlet means when inflated and to permit flow the liquid through the outlet means when in a deflated state, said boot including an open portion adjacent to the inlet means, and
   c. a hydrophobic filter element capable of repelling liquid but permitting the passage of air therethrough positioned over said open portion adjacent to the inlet means whereby liquid introduced to the housing the inlet means is passed through the housing for discharge from the outlet means and air introduced with the liquid is passed through the hydrophobic filter into the boot to stop the flow of liquid when the boot is inflated with air.

2. A valve as defined in claim 1 wherein the housing includes a generally cylindrical portion, with the housing including a frusto-conical portion adjacent to the inlet means integral with the cylindrical portion of the housing.

3. A valve as defined in claim 2 wherein the hydrophobic filter is centrally mounted adjacent to the frusto-conical portion, with the hydrophobic filter and the housing defining a flow path therebetween whereby liquid introduced to the housing through the inlet means is repelled by the hydrophobic filter and is passed through the flow paths for discharge from the housing through the outlet means.

4. A valve as defined in claim 1 which includes filter support means mounted on the cylindrical portion of the housing, said hydrophobic filter being mounted thereon, with the filter support means being dimensioned to define said flow paths between the filter support means and the cylindrical portion of the housing.

5. A valve as defined in claim 1 wherein the housing includes a second frusto-conical section adjacent to the outlet means, said second frusto-conical section defining a valve seat, with the boot including a lower portion corresponding, when inflated with fluid, to the valve seat whereby the boot forms a seal with the valve seat to prevent the flow of liquid through the outlet means.

6. In an administration set for the administration of intravenous liquids comprising a drip chamber adapted to receive intravenous liquid from a source of said liquid and administration means for infusing the liquid from the drip chamber to a patient, the improvement comprising a hydrophobic valve interposed between the drip chamber and said means, said hydrophobic valve comprising:
   a. a housing defining inlet means and outlet means, each of the inlet and outlet means communicating with the housing
   b. a resilient, inflatable boot mounted in the housing, said boot positioned to block the flow of liquid through the outlet means when inflated and to permit flow of liquid through the outlet means when in a deflated state, said boot including an open portion adjacent to the inlet means, and
   c. a hydrophobic filter element capable of repelling liquid but permitting the passage of air therethrough positioned over said open portion adjacent to the inlet means whereby liquid introduced to the housing through the inlet means is passed through the housing for discharge from the outlet means and air introduced with the liquid is passed through the hydrophobic filter into the boot to stop the flow of liquid when the boot is inflated with air.

7. A set defined in claim 6 wherein the housing includes a generally cylindrical portion, with the housing including a frusto-conical portion adjacent to the inlet means integral with the cylindrical portion of the housing.

8. A set defined in claim 6 wherein the hydrophobic filter is centrally mounted adjacent to the frusto-conical portion, with the hydrophobic filter and the housing defining a flow path therebetween whereby liquid introduced to the housing through the inlet means is repelled by the hydrophobic filter and is passed through the flow paths for discharge from the housing through the outlet means.

9. A set as defined in claim 6 which includes filter support means mounted on the cylindrical portion of the housing, said hydrophobic filter being mounted thereon, with the filter support means being dimensioned to define said flow paths between the filter support means and the cylindrical portion of the housing.

10. A set as defined in claim 6 wherein the housing includes a second frusto-conical section adjacent to the outlet means, said second frusto-conical section defining a valve seat, with the boot including a lower portion corresponding, when inflated with fluid, to the valve seat whereby the boot forms a seal with the valve seat to prevent the flow of liquid through the outlet means.

11. A set as defined in claim 6 which includes an in-line filter for filtering the intravenous liquid prior to infuring said liquid to a patient.

12. A set as defined in claim 6 the hydrophobic valve is integral with the drip chamber, and positioned at the lower end thereof whereby the hydrophobic vlave serves to shut from the drip chamer when said source empties.

* * * * *

UNITED STATES PATENT AND TRADEMARK OFFICE
CERTIFICATE OF CORRECTION

PATENT NO. : 3,993,062
DATED : November 23, 1976
INVENTOR(S) : Thurman S. Jess

It is certified that error appears in the above-identified patent and that said Letters Patent are hereby corrected as shown below:

Column 5, Line 46: after "housing", insert -- through --.

Column 6, Line 57: after "valve", insert -- seat --.

Column 6, Line 62: change "infuring" to -- infusing --.

Column 6, Line 63: after "6", insert -- wherein --.

Column 6, Line 64: after "and", insert -- is --.

Column 6, Line 65: change "vlave" to -- valve --.

Column 6, Line 66: after "shut", insert -- off liquid --.

Signed and Sealed this

Twenty-eighth Day of June 1977

[SEAL]

Attest:

RUTH C. MASON
Attesting Officer

C. MARSHALL DANN
Commissioner of Patents and Trademarks